US011071493B2

(12) United States Patent
Walker et al.

(10) Patent No.: US 11,071,493 B2
(45) Date of Patent: Jul. 27, 2021

(54) MULTICOMPONENT BRAIN-BASED ELECTROMAGNETIC BIOSIGNAL DETECTION SYSTEM

(71) Applicant: DREAMSCAPE MEDICAL LLC, Atlanta, GA (US)

(72) Inventors: Elijah Charles Walker, Silver Spring, MD (US); Anthony P. Kimani Mwangi, Fairburn, GA (US)

(73) Assignee: DREAMSCAPE MEDICAL LLC, Atlanta, GA (US)

( * ) Notice: Subject to any disclaimer, the term of this patent is extended or adjusted under 35 U.S.C. 154(b) by 193 days.

(21) Appl. No.: 16/152,778

(22) Filed: Oct. 5, 2018

(65) Prior Publication Data

US 2019/0029587 A1    Jan. 31, 2019

Related U.S. Application Data

(63) Continuation of application No. 15/165,309, filed on May 26, 2016, now abandoned, which is a continuation of application No. 14/062,573, filed on Oct. 24, 2013, now abandoned.

(60) Provisional application No. 61/790,007, filed on Mar. 15, 2013, provisional application No. 61/717,997, filed on Oct. 24, 2012.

(51) Int. Cl.
| | | |
|---|---|---|
| *A61B 5/00* | (2006.01) |
| *A61B 5/08* | (2006.01) |
| *A61B 3/113* | (2006.01) |
| *A61B 5/04* | (2006.01) |
| *A61B 5/0205* | (2006.01) |
| *A61B 5/0478* | (2006.01) |
| *A61B 5/242* | (2021.01) |

(52) U.S. Cl.
CPC ............ *A61B 5/4064* (2013.01); *A61B 3/113* (2013.01); *A61B 5/0022* (2013.01); *A61B 5/0205* (2013.01); *A61B 5/08* (2013.01); *A61B 5/242* (2021.01); *A61B 5/4818* (2013.01); *A61B 5/682* (2013.01); *A61B 5/6832* (2013.01)

(58) Field of Classification Search
CPC ......... A61B 5/6832; A61B 5/08; A61B 3/113; A61B 5/682; A61B 5/04005; A61B 5/4064; A61B 5/4818; A61B 5/0022; A61B 5/0205; A61B 5/04012
See application file for complete search history.

(56) References Cited

U.S. PATENT DOCUMENTS

| | | |
|---|---|---|
| 5,513,649 A | 5/1996 | Gevins et al. |
| 5,792,067 A * | 8/1998 | Karell ............... A61N 1/36034 |
| | | 600/534 |
| 6,263,225 B1 | 7/2001 | Howard, III |
| 7,173,437 B2 | 2/2007 | Hervieux et al. |
| 7,209,775 B2 | 4/2007 | Bae et al. |
| 7,328,062 B2 | 2/2008 | Rantala et al. |
| (Continued) | | |

FOREIGN PATENT DOCUMENTS

WO    WO/2013/026481 A1    2/2013

*Primary Examiner* — Christine H Matthews
*Assistant Examiner* — Joshua Daryl D Lannu
(74) *Attorney, Agent, or Firm* — Polsinelli PC

(57) ABSTRACT

Systems and methods detect a multicomponent brain-based bio-signal in non-brain internal body tissues and cavities of a patient, such as the mouth. Sub-component signals are filtered from the multi-component signal to isolate frequency brave wave bands.

20 Claims, 15 Drawing Sheets

(56) References Cited

U.S. PATENT DOCUMENTS

| | | |
|---|---|---|
| 7,693,566 B2 | 4/2010 | Newman et al. |
| 8,019,402 B1 | 9/2011 | Kryzpow et al. |
| 8,150,523 B2 | 4/2012 | Schiff |
| 8,161,971 B2 | 4/2012 | Jaffe et al. |
| 8,190,248 B2 | 5/2012 | Besio et al. |
| 8,209,004 B2 | 6/2012 | Freer et al. |
| 8,224,434 B2 | 7/2012 | Greene |
| 8,267,862 B2 | 9/2012 | Jeong et al. |
| 8,391,948 B2 | 3/2013 | Causevic et al. |
| 8,391,967 B2 | 3/2013 | Freer et al. |
| 8,437,843 B1 | 5/2013 | Kayyali et al. |
| 8,447,392 B2 | 5/2013 | Llinas |
| 8,447,406 B2 | 5/2013 | Wu et al. |
| 8,454,505 B2 | 6/2013 | Yazicioglu et al. |
| 8,466,875 B2 | 6/2013 | Nakada et al. |
| 2005/0239493 A1 | 10/2005 | Batkin et al. |
| 2007/0032737 A1 | 2/2007 | Causevic et al. |
| 2007/0106172 A1 | 5/2007 | Abreu |
| 2008/0058620 A1 | 3/2008 | Lee et al. |
| 2008/0300469 A1* | 12/2008 | Kuo .................. A61B 1/00165 600/300 |
| 2009/0082829 A1 | 3/2009 | Panken et al. |
| 2010/0274152 A1 | 10/2010 | McPeck et al. |
| 2011/0245633 A1 | 10/2011 | Goldberg et al. |
| 2012/0029399 A1 | 2/2012 | Sankai |
| 2012/0041330 A1 | 2/2012 | Prichep et al. |
| 2012/0065478 A1 | 3/2012 | Lin et al. |
| 2012/0133363 A1 | 5/2012 | Mareci et al. |
| 2012/0172682 A1 | 7/2012 | Linderman et al. |
| 2012/0253166 A1 | 10/2012 | Ahn et al. |
| 2012/0294451 A1 | 11/2012 | Kozuka et al. |
| 2012/0302867 A1 | 11/2012 | Ichimura |
| 2012/0330178 A1 | 12/2012 | Kraft et al. |
| 2013/0018251 A1 | 1/2013 | Caprio et al. |
| 2013/0035578 A1 | 2/2013 | Chiu et al. |
| 2013/0079634 A1 | 3/2013 | Kerber |
| 2013/0116520 A1 | 5/2013 | Roham et al. |
| 2013/0184316 A1 | 7/2013 | Hornstein |
| 2013/0211270 A1 | 8/2013 | St. Laurent et al. |
| 2013/0253286 A1 | 9/2013 | Fridman |

\* cited by examiner

MULTICOMPONENT BRAIN-BASED ELECTROMAGNETIC BIOSIGNAL DETECTION SYSTEM

CROSS REFERENCE TO RELATED APPLICATIONS

The present application is a continuation of U.S. application Ser. No. 15/165,309 filed May 26, 2016, which is a continuation of U.S. application Ser. No. 14/062,573 filed Oct. 24, 2013, which claims the benefit of priority of U.S. Provisional Application No. 61/717,997 filed Oct. 24, 2012, and of U.S. Provisional Application No. 61/790,007 filed Mar. 15, 2013, all of which are incorporated herein by reference.

FIELD OF THE INVENTION

The present invention relates to methods of reading brain-based bio-signals. In non-limiting embodiments the present invention provides a method for detecting, processing and extracting a variety of biosignals from a brain-based multi-component signal detected in the oral cavity.

BACKGROUND OF THE INVENTION

Using electroencephalogram ("EEG") sensors positioned on the scalp to detect brain activity has been known in the art since the 1920's. As the electrical field generated by brain activity is very small, it can only be recognized by EEG if large assemblies of neurons show a similar behavior. The resulting neural EEG signals are in the range of micro-volts (μV) and may be easily be masked by interfering artificial sources causing artifacts in the signal. Typically, artifacts in an EEG signal are caused either by the non-neural physiological activities of the subject or by external technical sources. Non-neural physiological activities may include eye blinks, eye movements, muscle activity in the vicinity of the head (e.g. face muscles, jaws, tongue, neck), heartbeat, pulse and Mayer waves, and the like. External technical sources may include swaying cables in the magnetic field of the earth, improper grounding, power supplies or transformers, radio waves and the like.

Other ways to monitor brain electrical activity rely on invasive procedures including needle electrodes (sharp wires placed between the scalp and the skull); cortical electrodes, subdural electrodes and depth electrodes. The characteristics of brain electrical activity monitored with invasive electrodes are related to surface electrodes like EEG electrodes on the scalp or skin, but are different since attenuation and spreading of the signal by the scalp and skin is bypassed.

Thus it is desirable to detect and monitor brain activity and brain-based bio-signals with little interference from other electrical sources and without requiring invasive procedures.

The description herein of certain advantages and disadvantages of known methods and devices is not intended to limit the scope of the present invention. Indeed, the present embodiments may include some or all of the features described above without suffering from the same disadvantages.

SUMMARY OF THE INVENTION

In view of the foregoing, it is a feature of the embodiments described herein to provide a method for monitoring electromagnetic activity in the brain via the oral cavity without using invasive procedures. Particular brain-based electromagnetic bio-signals can include multiple component signals forming a multicomponent brain-based signal, that may include signals that are generated from other parts of the body including the central nervous system, heart electrical activity, lung activity (respiration), local artery movement, eye dipole electrical activity (and other dipoles), muscle electrical activity, and local tissue electrical activity such as generated by the peripheral nervous system, as well as brain-based electromagnetic signals. The multicomponent brain-based signal may be detected by sensors positioned in the oral cavity. The multicomponent brain-based signal may then be digitized, amplified and filtered. After filtering desired sub-component bio signals may be isolated from the multicomponent brain-based signal for further analysis.

For the purposes of this invention, "multicomponent brain-based signal" is used to describe this collection of sub-component bio-signals, as the primary component bio-signals of interest emanates from the brain. The multicomponent brain-based signal can include bio-electromagnetic signals, cardiac bio-electromagnetic bio-signals, local tissue bio-electromagnetic signals; eye dipole bioelectric bio-signals; muscle bio-electromagnetic bio-signals; tongue bio-electromagnetic bio-signals; cardiac related pulsatile bio-signals; respiration related pulsatile bio-signals; movement related bio-signals; biomechanical bio-signals; bio-acoustic bio-signals. The component signals of the multicomponent brain-based signal are important for many applications (e.g. medical, veterinary and non-medical applications). Due to the brain-based signal detector(s) of this invention being located in the oral cavity, the detector(s) may detect electrical activity from many parts of the brain that includes the cerebral cortex, as well as other parts of the brain.

DETAILED DESCRIPTION OF THE INVENTION

The following description is intended to convey a thorough understanding of the embodiments by providing a number of specific embodiments and details involving methods for detecting and processing brain-based multi-component signals in an oral cavity. It is understood, however, that the invention is not limited to these specific embodiments and details, which are exemplary only. It is further understood that one possessing ordinary skill in the art, in light of known devices, systems and methods, would appreciate the use of the invention for its intended purposes and benefits in any number of alternative embodiments.

In a preferred embodiment of the invention a system for detecting multi-component brain-based electromagnetic bio-signals includes a sensor in the oral cavity may be coupled to one or more electronic processors capable of electronically digitizing, amplifying, attenuating, filtering and normalizing the multi-component brain-based bio-signals as needed. The computer processor may also be capable of extracting, isolating or otherwise dividing sub-component signals from the multi-component brain-based bio-signals, and optionally classifying and analyzing the sub-component signals.

The sensor may be an electrical or magnetic sensor capable of detecting multi-component brain-based electromagnetic bio-signals. In a preferred embodiment the sensor includes electrodes touching the hard palate, where one electrode acts as a reference for comparison with one or more other electrodes.

The electrodes may be resistive mode electrodes, capacitive mode electrodes, current mode electrodes, or inductive mode electrodes. The electrodes may be passive electrodes which simply receive a signal, or may be active electrodes which are able to digitize or otherwise process the received signal with an internal electronic processor.

In some embodiments the sensor in the oral cavity may be included in an oral device configured to couple to the dentition or other oral tissue. In further embodiments the position of the sensor or electrodes of the sensor may be adjustable in relation to the oral device.

In some embodiments the sensor may be communicatively coupled to a processor in the oral device. In other embodiments the sensor may be communicatively coupled to one or more external processing device. The sensor and/or processor(s) may be communicatively coupled via wires and/or wirelessly, such as Bluetooth or other wireless technology.

Figure 1:
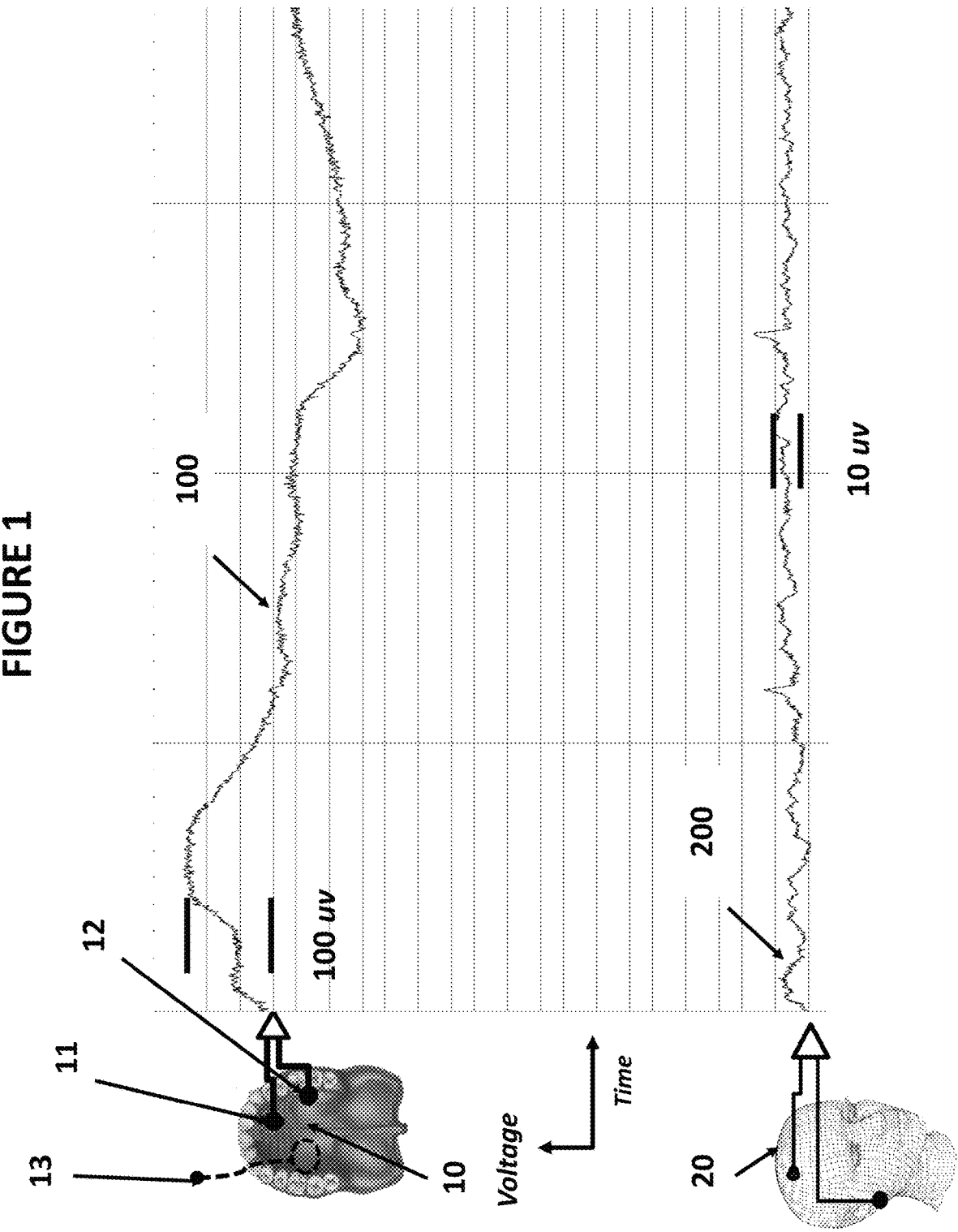
FIG. 1 is a comparative schematic view of hard palate multicomponent brain-based bio-signal detection versus scalp EEG brain wave detection.

FIG. 1 is a comparison of the hard palate 10 multicomponent brain-based bio-signal 100 versus a standard scalp EEG brain wave signal. A sensor including reference electrode 11 and left signal electrode 12 coupled or proximate to hard-palate 10 are used to detect the multicomponent brain-based bio-signal 100. In some embodiments the sensor may also include right signal electrode 13. The multicomponent brain-based bio-signal 100 is the raw hard palate bio-potential signal. The raw unfiltered scalp EEG signal 200 is detected from the F4A2 electrode 20 (F=frontal, 4=right side of scalp by 10-20 standards) with a reference electrode on the right mastoid. The multicomponent brain-based bio-signal 100 is a relatively unremarkable pattern of the raw hard palate bio-potential signal in comparison to the raw scalp EEG signal 200. The multicomponent brain-based bio-signal 100 has a significantly larger voltage range when compared to raw scalp EEG signal 200, 100 μV versus 10 μV respectively. This demonstrates that special analysis of the hard palate 10 multicomponent brain-based bio-signal 100 is necessary to determine subcomponents of the hard palate 10 multicomponent brain-based bio-signal 100 especially the brain-based subcomponent signals.

The reference electrode 11 was placed on the hard palate 10 to avoid mixing of scalp EEG with oral brain-based signals. Left signal electrode 12 and right signal electrode 13 may be gold or gold plated electrodes covered in cotton gauze. Saline may be used in some embodiments to wet the gauze.

Figure 2:
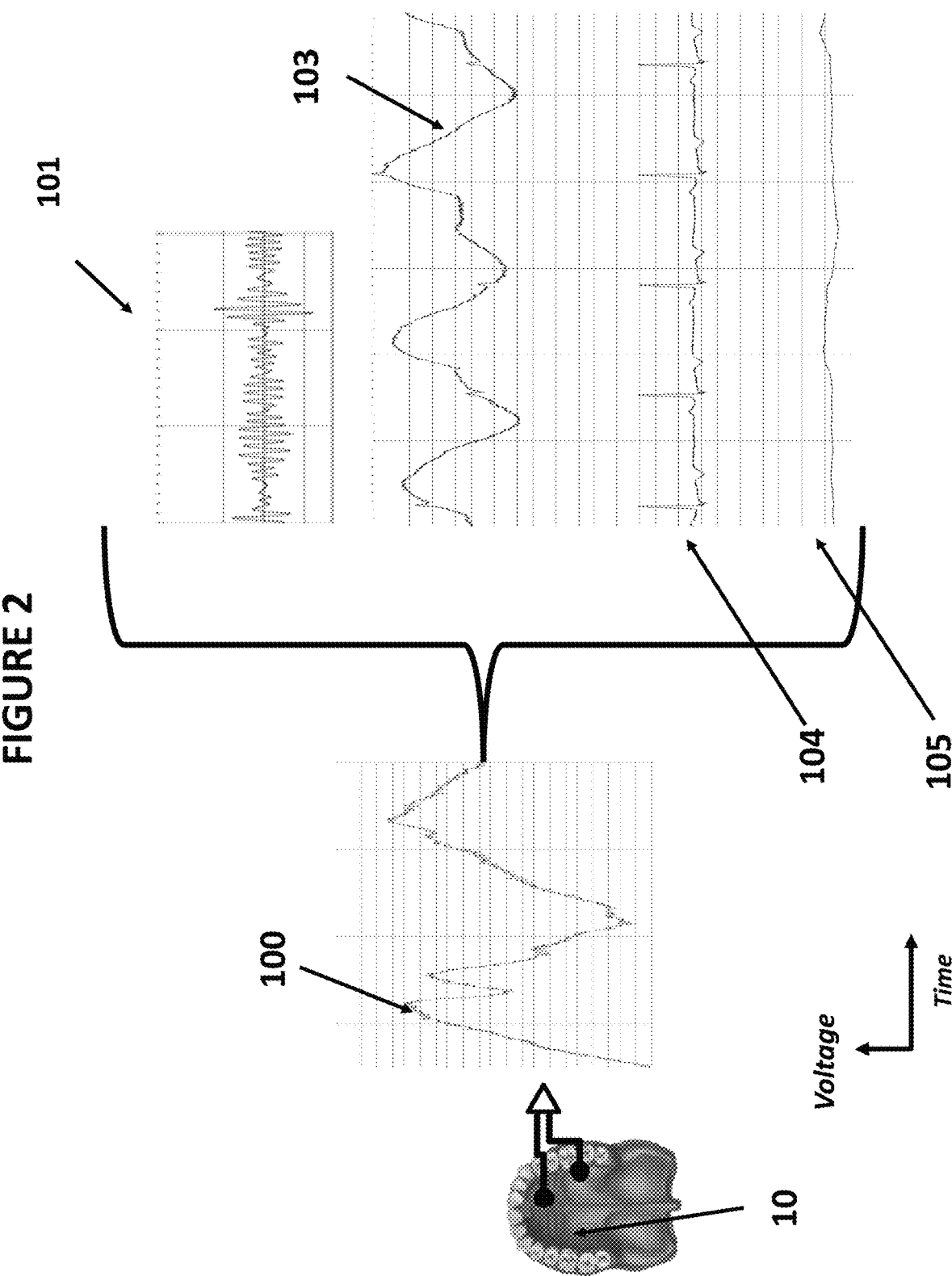
FIG. 2 is a schematic view of the hard palate multicomponent brain-based bio-signal and the resulting subcomponent waves after extraction.

FIG. 2 shows the hard palate 10 multicomponent brain-based bio-signal 100 being split into its various subcomponent signals after being processed according to embodiments of this invention. The subcomponent signals may include an 8-14 Hz brain wave subcomponent signal 101, an eye movement subcomponent signal 103, a cardiac subcomponent signal 104 and a respiration subcomponent signal 105.

Figure 3:
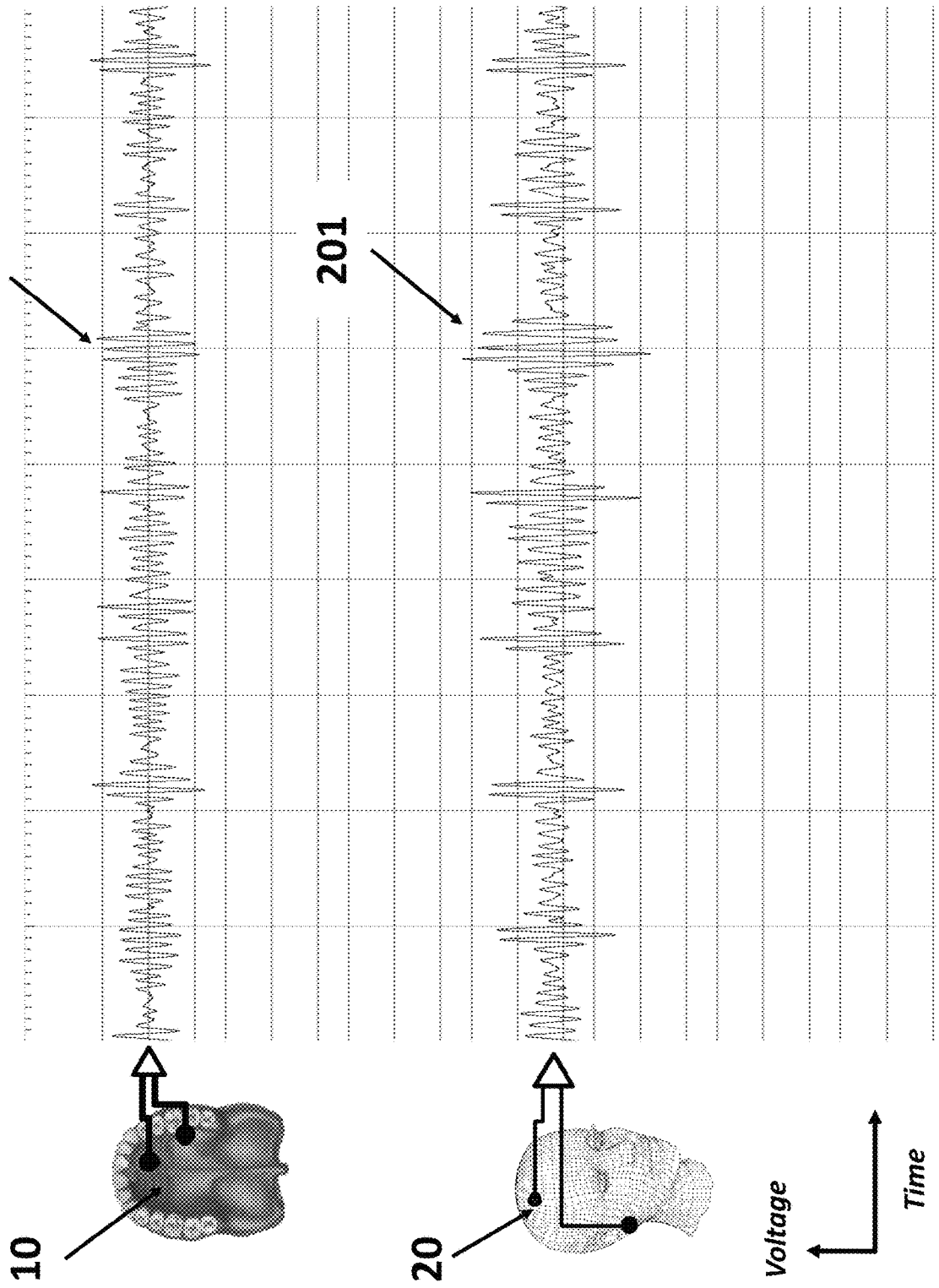
FIG. 3 is a comparative schematic view of an extracted hard palate alpha wave subcomponent signal versus scalp EEG alpha waves.

FIG. 3 shows the strong correlation between the 8-14 Hz brain wave subcomponent signal 102 detected on the hard palate and the 8-14 Hz brain wave scalp EEG signal 201.

Figure 4:
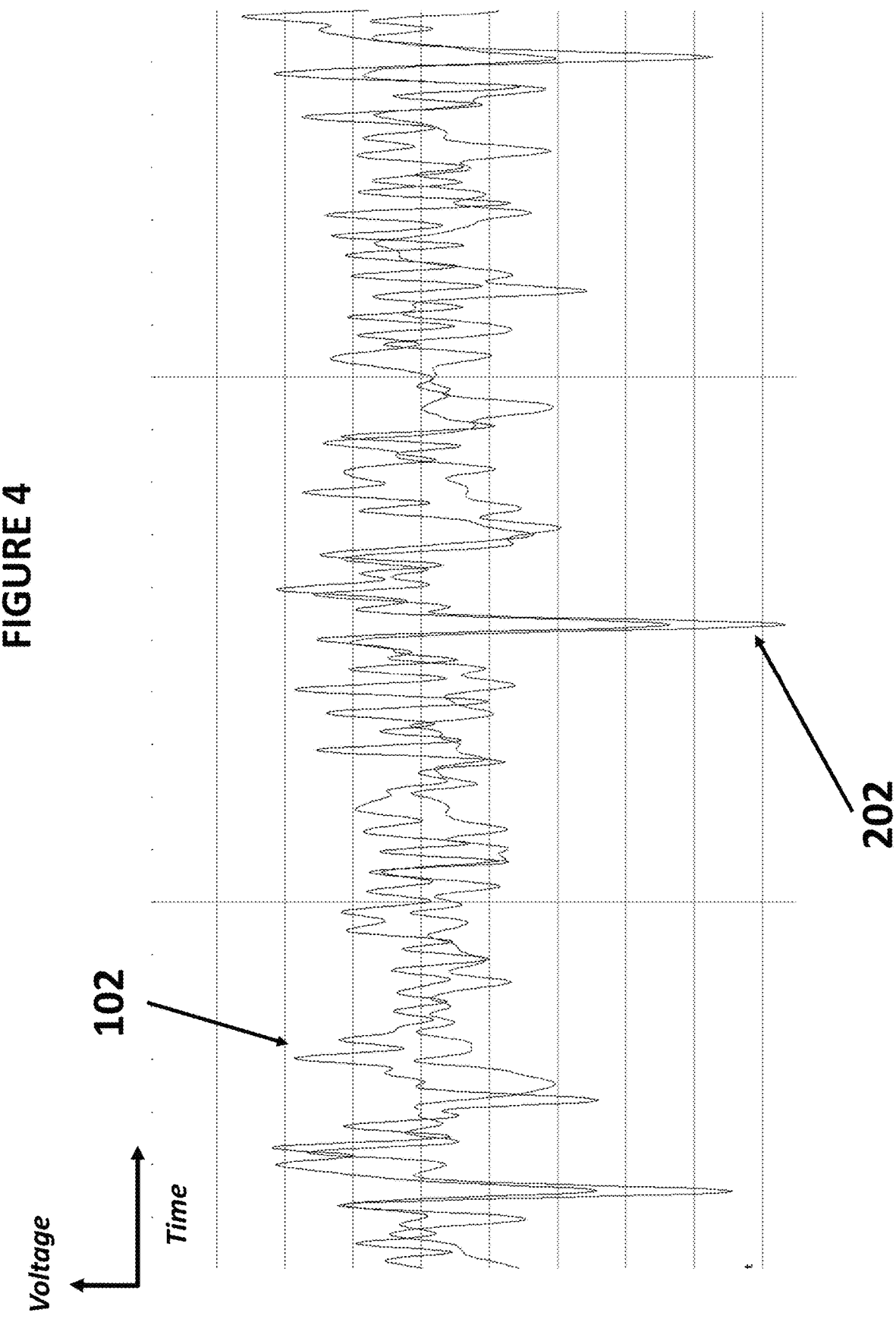
FIG. 4 is an overlay schematic view of an extracted hard palate brain-based bio-signal subcomponent signal versus scalp EEG brain waves during mental counting activity.

FIG. 4 shows the strong correlation between the 3.5-30 Hz brain wave subcomponent signal 102 detected on the hard palate and the 3.5-30 Hz brain wave scalp EEG signal 202 of a subject when subject was performing the mental activity of counting backwards from 100 by 7's (i.e. 100, 93, 86, 79, etc.). The subject was seated in a well-lit, environmentally controlled room.

Figure 5:
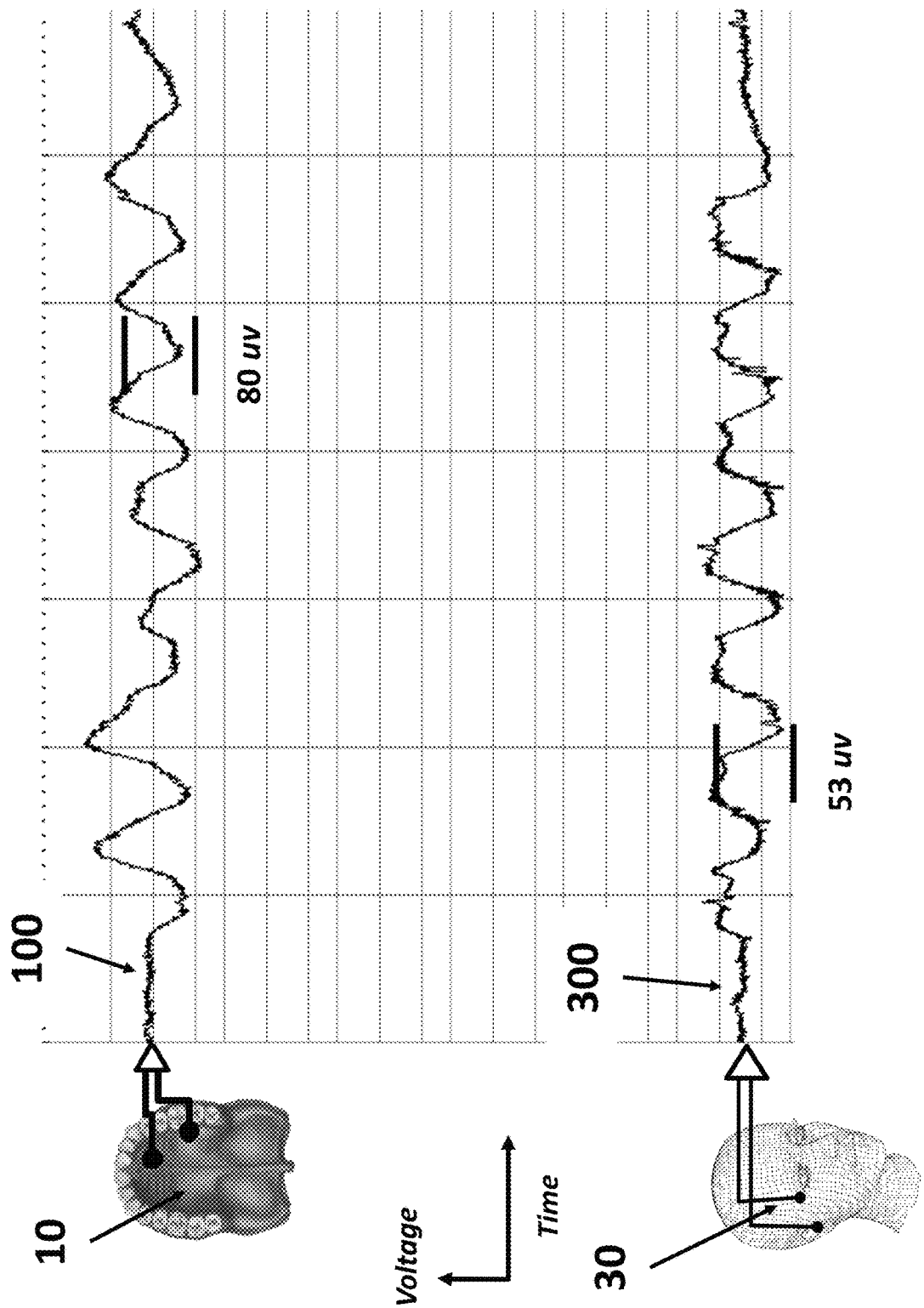
FIG. 5 is a comparative schematic view of an extracted hard palate brain-based bio-signal subcomponent signal versus raw EOG brain waves during up-down eye movement.

FIG. 5 shows the strong correlation between an 80 μV range multicomponent brain-based bio-signal 100 detected on the hard palate 10 and the 53 μV brain wave EOG signal 300 detected with EOG electrodes 30 on the right-side human scalp while the subject was quickly looking up and down. No filtering or isolation of subcomponents of the multicomponent brain-based bio-signal 100 was needed for this embodiment.

Figure 6:
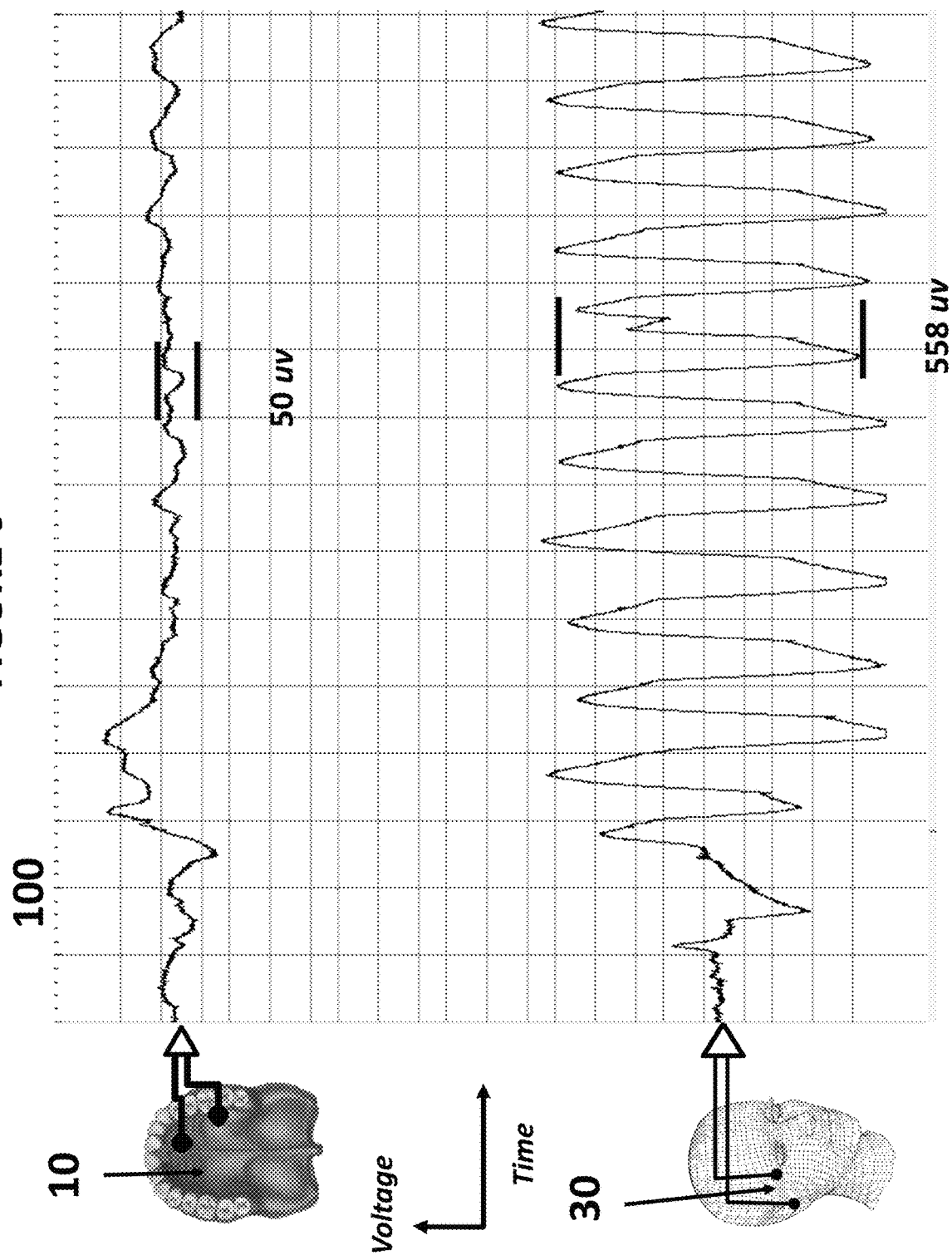
FIG. 6 is a comparative schematic view of an extracted hard palate brain-based bio-signal subcomponent signal versus raw EOG brain waves during left-right eye movement.

FIG. 6 shows the correlation between an 50 μV range multicomponent brain-based bio-signal 100 detected on the hard palate 10 and the 558 μV brain wave EOG signal 300 detected with EOG electrodes 30 on the right-side human scalp while the subject was quickly looking left and right. No filtering or isolation of subcomponents of the multicomponent brain-based bio-signal 100 was needed for this embodiment.

Figure 7:
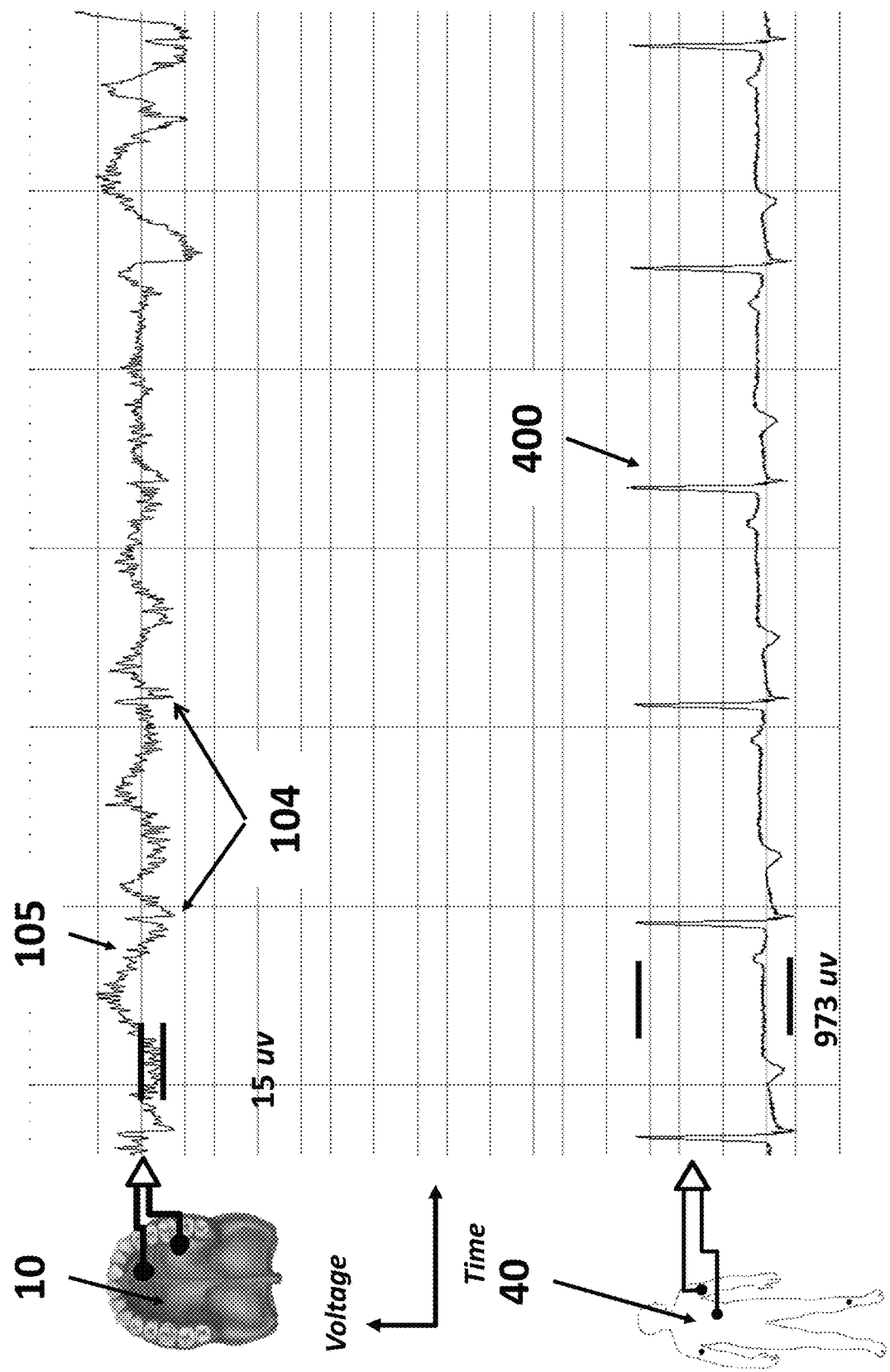
FIG. 7 is a comparative schematic view of an extracted hard palate brain-based bio-signal subcomponent signal versus cardiac ECG waves.

FIG. 7 shows the correlation between cardiac signals detected at 0.5-249 Hz in the brain wave subcomponent signal 104 on the hard palate 10 and the cardiac signals in an unfiltered ECG signal 400 detected with ECG electrode 40. The subject was seated in a well-lit, environmentally controlled room during recording. The multicomponent brain-based bio-signal 100 was filtered this application to remove DC offset.

Figure 8:
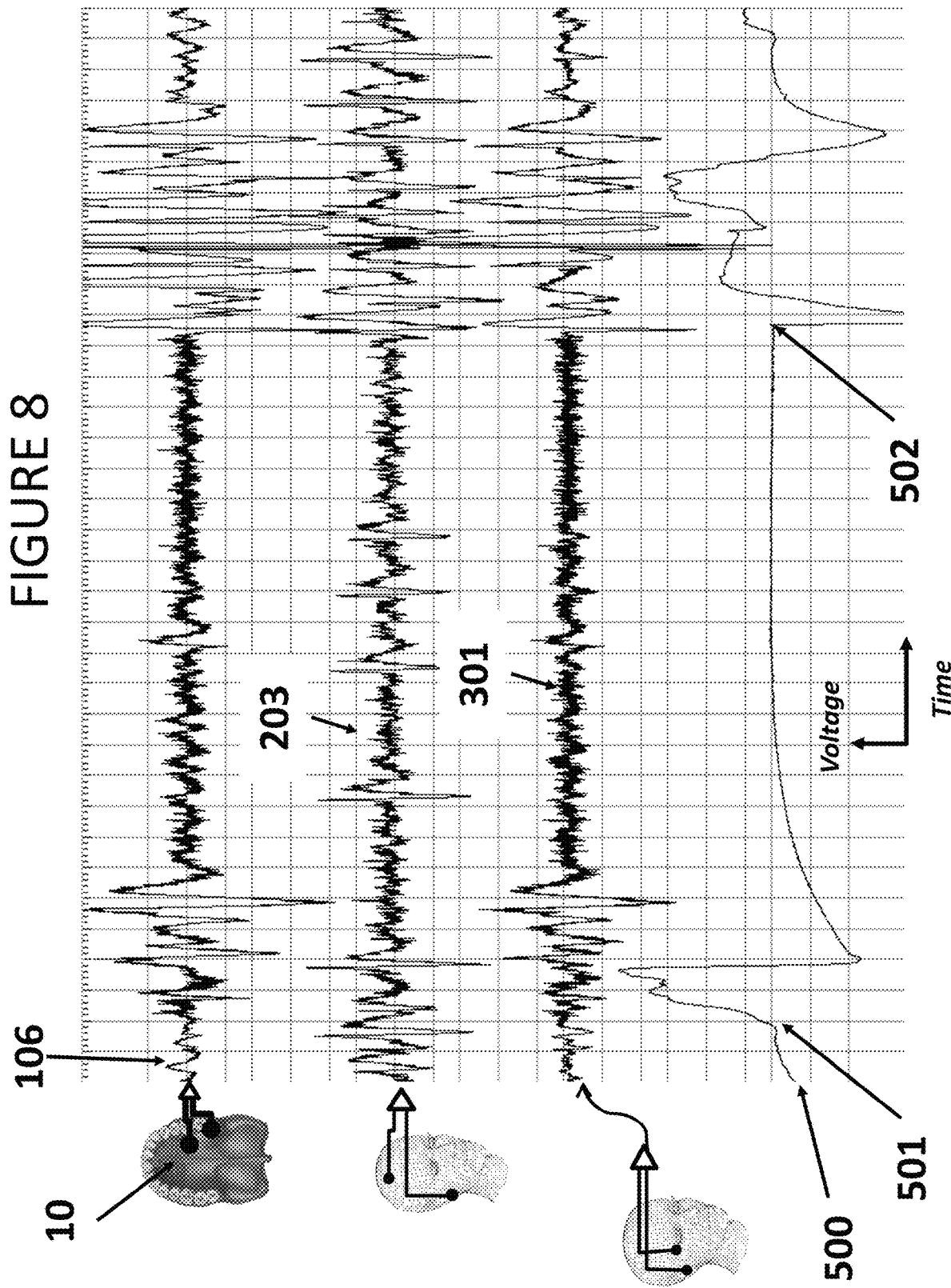
FIG. 8 is a comparative schematic view of an extracted hard palate brain-based bio-signal subcomponent signal versus EEG, EOG and Respiration waves.

FIG. 8 shows the correlation between respiration sub component signals 106 at 1.5 Hz-249 Hz extracted from the brain-based multicomponent bio-signals detected on the hard palate 10 and scalp EEG signals 203, right eye EOG signals 301 both of which were filtered at 1.5 Hz-249 Hz, and a nasal cannula respiration signal 500 while the subject takes a fast deep breath 501 and holds the breath 502 for 20 seconds. The graph shows that the hard palate bio-potential changes at the same time the scalp EEG and EOG changes showing the strong temporal relation between the hard palate multicomponent bio-signals and the scalp related signals.

Figure 9:
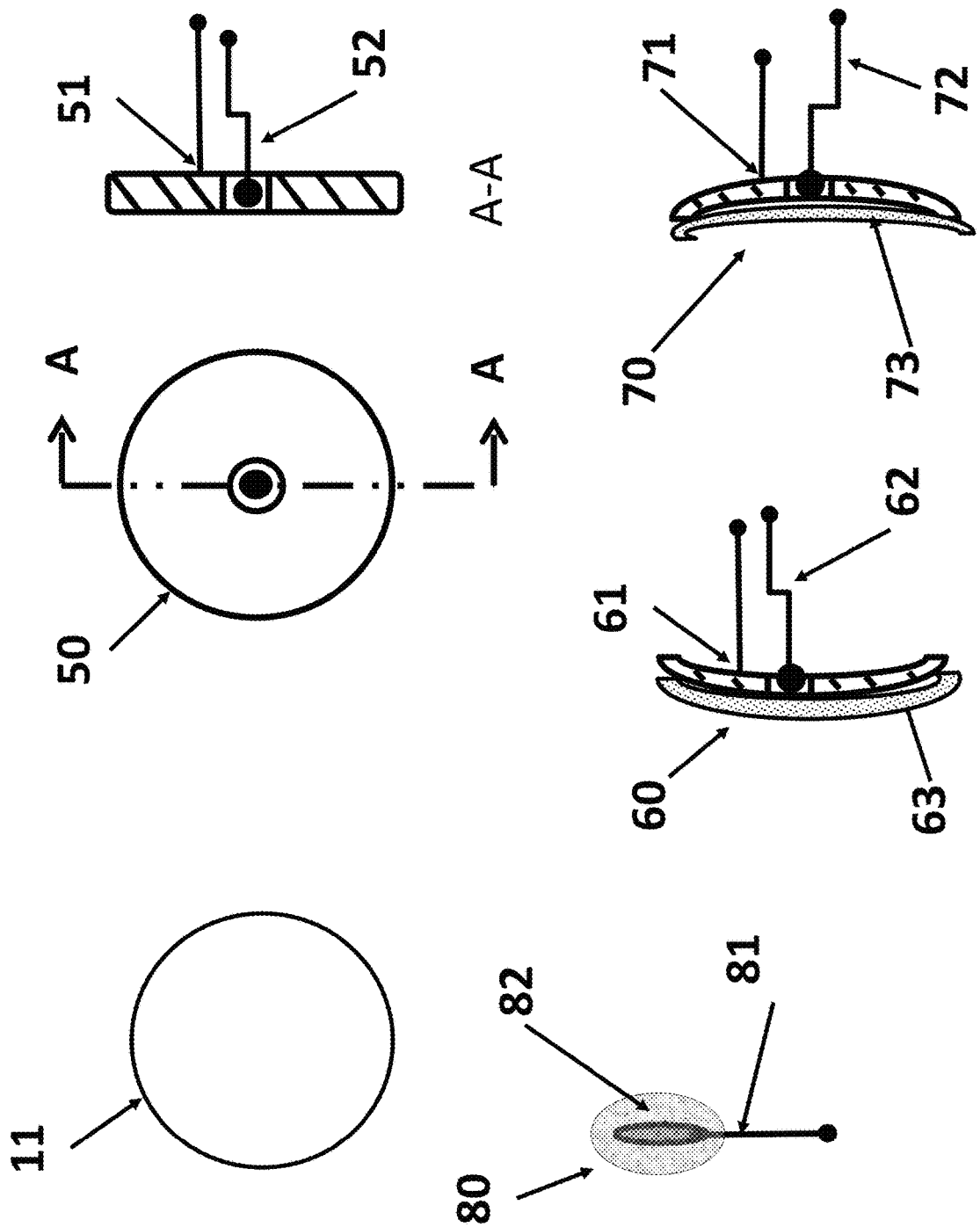
FIG. 9 is schematic views of various embodiments of the electrodes of the invention.

FIG. 9 shows various electrode embodiments for use in hard palate multicomponent bio-signal detection to accommodate the shape of oral tissue and provide for comfort and biocompatibility. Soft materials (gauze, or foam) may provide mechanical safety and maintains electrolytes around the electrode. Other materials can be used for electrodes as desired. The electrode assembly 50 includes a metal electrode 51 and temperature sensor 52. The combination of electrode 51 with temperature sensing 52 for the oral cavity, or other body locations, is shown. The electrodes detect current flow from tissue and the temperature sensor allows determination of oral temperature, motion artifact (since temperature is not a bio-potential measurement), and oral airflow. Average oral temperature can be estimated by a thermistor, semiconductor IC, thermocouple, or other appropriate sensor. Variations in temperature arising from airflow can be used to determine the presence/absence of airflow as part of pre-processing or by the microcontroller (μCU). One embodiment of the electrode may be a convex electrode assembly 60 which may include a metal electrode with a lead wire 61 and temperature sensor 62 and a soft, absorbent cover-surface 63. Another embodiment of the electrode may be a concave electrode assembly 70 which may include a metal electrode with a lead wire 71 and temperature sensor 72 and a soft, absorbent cover-surface 73. A third embodiment of the electrode may be a flat electrode assembly 80 which may include a metal electrode with a lead wire 81 and a soft, absorbent cover 82. The reference electrode 11, may be a circular metal electrode.

Figure 10:
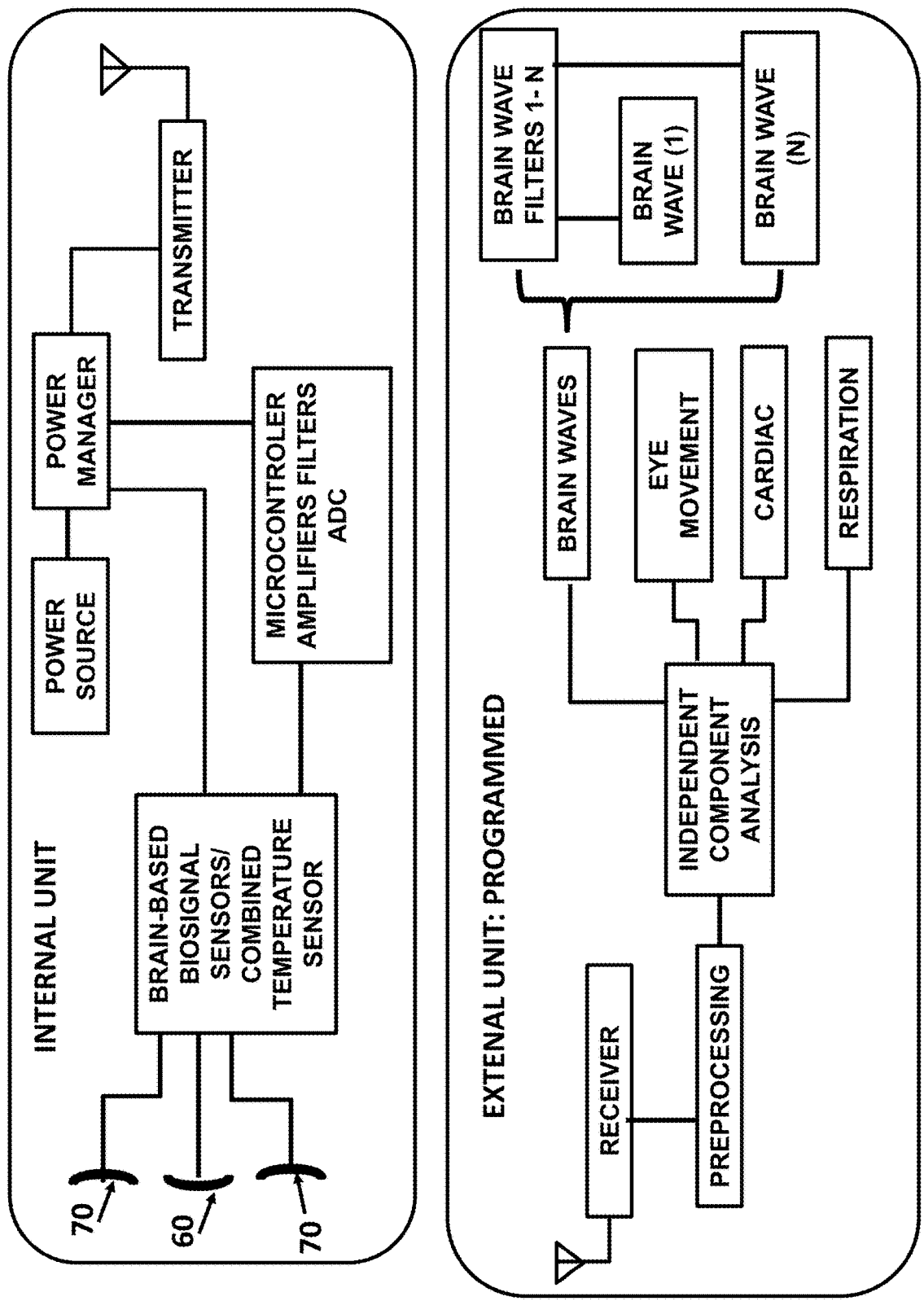
FIG. 10 is a schematic view a system to detect sleep disorders including internal and external units.

FIG. 10 is a schematic of a system to detect sleep disorders 600 including an internal oral unit 601 and an external unit 650. The internal oral unit 601 may include a convex electrode 60 positioned near the middle of the hard palate and one or two concave electrodes 70 positioned to the left and/or right near the gums.

The internal oral unit 601 may include a sensor unit 602, a power source 603, a power manager 604, a microcontroller 605, and a transmission unit 606. The internal oral unit 601 may amplify, filter and/or digitize multicomponent bio-signals using dedicated circuitry as shown or as part of the data-management microcontroller (μCU). Digital signals may be passed to a radio-frequency (RF) module for transmission to a remote receiver, e.g., a Smartphone or computer, or cloud etc.

Detecting multicomponent brain-based signals may be accomplished by placing the internal unit 601 inside the appropriate body cavity where brain-based multicomponent bio-signal detection can automatically (or manually) be initiated. Signal detection usually begins immediately, however a temperature sensing component can be added to monitor environmental temperatures to ensure proper operating conditions and or monitor temperature during data collection. The temperature sensor can also be used to monitor changes in airflow via the mouth. Additional sensors can also be added to monitor a variety of additional physiological variables including oxygen saturation via optical PPG sensor/monitor, accelerometer, gyroscope, GPS, pressure, camera, biological or chemical monitors etc. Brain-based Detectors monitor multiparameter physiological signals including brain waves.

The detector (i.e. sensor) can be based on any of the following sensors: resistance mode electrodes, capacitive mode electrodes, current mode electrodes, passive electrodes, active electrodes, magnetic mode detectors, inductive mode detectors, acoustic mode detectors, optical or electro-optic mode detectors, chemical or biochemical mode detectors, biological mode detectors and brain-based detector arrays (brain-based detector can also comprise multiple sensors oriented in different geometric planes). The sensors may be of various shapes and include various metals, metal salts, or metal alloys, semiconductors, polymers, carbon compounds, conductive fabrics, composites, graphenes, non-metals; sensor comprises rigid, semi-rigid, and other flexible materials. The sensors may utilize microelectronics technology. The sensors may be disposable and/or reusable. The sensors may include remote sensors. Sensors may be adjustable in position and/or performance to optimize brain-based multicomponent bio-signal detection.

Sensor unit 602 may detect electrical signals from the hard palate picked up by electrodes and may amplify and filter the electrical signals to remove motion and other artifacts and conveyed to the microcontroller (μCU) 605 via the SPI bus for further processing, storage and transmission.

Signal and power management scheduling are performed by the μCU 605. Energy consumed from a disposable or rechargeable power supply 603 can be minimized by the μCU 605 by controlling the duration and duty cycle of data-collection devices, the transmission module 606, and the μCU 605 itself. Intelligent power management can reduce the size and complexity of the power source 603 and eliminate the need for a power line-operated system.

Data transmission by the transmission unit 606 may be via well-known standard communications protocols, such as Bluetooth (BT) and Bluetooth LE (Low Energy) (BLE), or a proprietary protocols or frequencies. Use of standard protocols may ensure easier post-transmission processing. The transmission unit 606 may support both BT and BLE, which can be accessed by Smartphones and other devices. An antenna of the transmission unit 606 may be built into the side and/or front walls of an oral appliance attachment device as shown in FIGS. 12-15.

The external unit 650 includes a receiver unit 651, a preprocessing unit 652, an Independent Component Analysis ("ICA") processor 700, a raw brain-based multicomponent bio-signal component analyzer 750, The receiver unit 651 may be configured to receive signals from the transmission unit 606. The preprocessing unit 652 removes as much signal noise as possible The ICA processor 700 may use standard ICA algorithms to extract and isolate individual subcomponent signals. To ensure a good estimate of the components of the brain-based raw hard palate signal, brain wave filters 1-N 751, 752 and 753, eye movement signal processor 710, cardiac signal processor 720 and respiration signal processor 730.

To ensure a good estimate of the subcomponents of the brain-based raw hard palate multicomponent bio-signal it's important to remove as much signal noise as possible with a preprocessing unit 652. The preprocessing unit 652 may eliminate non-physiological noise via filtering and sensors (thermistors) built into electrodes or a sensor platform. Electrodes may be shielded on their rear surface by the oral attachment device to prevent disturbance by the tongue and or internal facial muscles. Thermistors also provide a means to detect movement of the device relative to tissue as well as provide means to correct for large temperature changes due to breathing. Additional processing includes data filtering such as low pass filtering. Additional preprocessing may include centering and whitening. Centering removes the mean from each component by subtracting the mean of the data from the actual data. Whitening the data is done to make the raw data uncorrelated to ensure that each subcomponent is as independent as possible. Preprocessing can also identify eye movements due to the unique arrangement of the electrodes (left and right) that produce significant differences in the raw signal detected by each electrode. Root mean square values can be determined and threshold detectors may be incorporated.

Digitization by the pre-processing unit 652 may be electronically performed to enable efficient digital processing as well as signal amplification and or attenuation of the bio-signals if necessary. Pre-processing also seeks to remove unwanted noise by filtering, shielding, blocking, or algorithmically removing or eliminating undesirable physiological and or non-physiological signals such as electrical noise, acoustical noise, mechanical noise, other artifact, or galvanic currents from dissimilar metals, or tongue artifact etc. Undesirable artifact contained in biosignals can hamper recordings. Signal normalization can also occur at this stage.

The ICA processor 700 determines the individual subcomponent signals of the raw hard palate multicomponent bio-signal without previously knowing each component. To effectively determine each subcomponent the number of detectors (sensors) must be equal to or greater to the number of individual signal components. Embodiments may utilize three electrodes to detect bio-potentials each with a built-in thermistor which provides six (6) detectors overall. This embodiment may detect 4 subcomponent bio-signals. To separate the components the JADE algorithm (Joint Approximate Diagonalization Eignen Matrices), which tends to perform best for small datasets) can be incorporated used by the ICA processor 700 of a computer or Field Programmable Gate Array (FPGA).

Extracting, isolating, or dividing the detected multicomponent brain-based signal into individual parasubcomponent signals may involve appropriate means to extract, isolate, and/or divide the brain-based multicomponent signal into constituent physiological signals and/or other signals as desired.

Primary subcomponent signals may include brain-based bio-electromagnetic signals, cardiac bio-electromagnetic bio-signals, ECG, local tissue bio-electromagnetic signals; eye dipole bioelectric bio-signals, muscle bio-electromagnetic bio-signals, tongue bio-electromagnetic bio-signals, cardiovascular related pulsatile bio-signals (e.g. Blood Volume Pulse); respiration related pulsatile bio-signals, movement related bio-signals, biomechanical bio-signals and/or bio-acoustic bio-signals. Each subcomponent signal typically includes multiple frequencies, and may have different dynamic ranges that may overlap. In some embodiments additional physiological parameters can be derived, including heart rate, respiration rate, heart rate variability, pulse transit time, arterial blood pressure.

A variety of signal processing or signal analysis means (implemented in algorithms) can be utilized to extract the subcomponent bio-signals described. Subcomponent bio-signal extraction may include use of pattern recognition, Independent Component Analysis, Principle Component analysis, Linear analysis, Frequency domain analysis, time—frequency and non-linear techniques such as correlation dimension (CD), phase space plots, different entropies, wavelet based, Hilbert-Huang Transforms (HHT), and similar means as desired.

For some applications, signal isolation or extraction may not be required. For example, eye movement signals tend to be larger than other oral signals so for eye movement applications extracting other signals may not be required.

In some embodiments key subcomponent signal features, such as data points, thresholds and/or data slope be extracted or isolated from the signal of interest. This may involve identification of brain-based signal patterns and translation into commands to extract said feature and or issue commands to perform a task. A desired algorithm may be used to automatically estimate/calculate a value to represent the signals by a few relevant key values. There are a large variety of algorithms that may be implemented from the simplistic methods such as adding, subtracting, multiplying, dividing, etc., to other complex techniques involving time-based approaches or frequency based approaches, Principle component analysis, Support vector machine, Genetic algorithm, Distinctive sensitive learning vector quantization etc.

In some embodiments key features of a subcomponent bio-signal may be classified or translated to a command. The classification step assigns a class to a set of features extracted from the signals. The class can correspond to the type of mental states identified. This step can also be denoted as "feature translation".

Key feature information may be provided or displayed to a user/operator and/or used to perform tasks, such as comparing an extracted subcomponent bio-signals to a database of baseline signals to control a device, assist in a diagnosis of a disease, disorder, or condition, and or report the status of the device function.

Following subcomponent bio-signal extraction, individual subcomponent bio-signals can be displayed or utilized for other purposes such as calculating vital signs, part of a command to control another device(s), or to perform additional processing such as extract particular features.

Following separation into individual subcomponent signals the raw brain-signal can be further analyzed or separated into various frequency bands using band-pass filters 750 and then displayed or used to issue a command. This may include brain wave filters 1-N 751. The filters may be programmed or maintained in hardware for bands of interest 752, 753.

Eye movement sub component signals 710 can be displayed and observed for Rapid Eye Movement (REM) to determine sleep stage.

Cardiac signals 720 can show basic heart rate and can be used to determine R wave peaks as well as heart rate variability.

Respiration signals 730 can be displayed to determine breathing rate.

Various data may be stored on a data storage device incorporated into the internal oral unit and/or external unit.

In some embodiments of the system may also include a stimulate tissue device.

In some applications brain-based biosignal maps can be developed to allow for topographical mapping of electrical activity for internal body locations.

Figure 11:
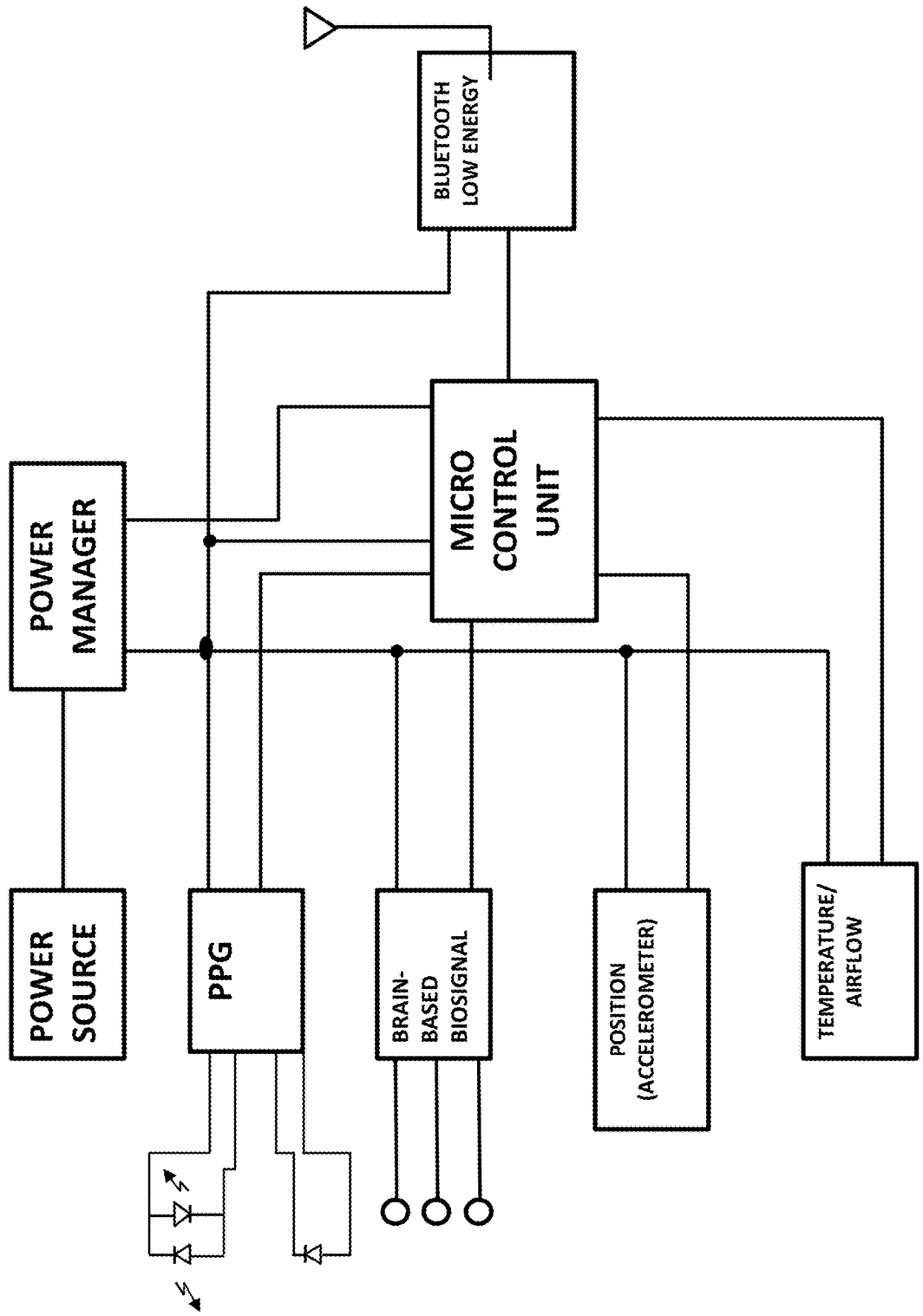
FIG. 11 is schematic view of an alternative embodiment multi-sensor system.

An alternative embodiment that incorporates multiple sensors such as oxygen saturation, head position via accelerometers, temperature, and brain-based signals is shown in FIG. 11.

Figure 12:
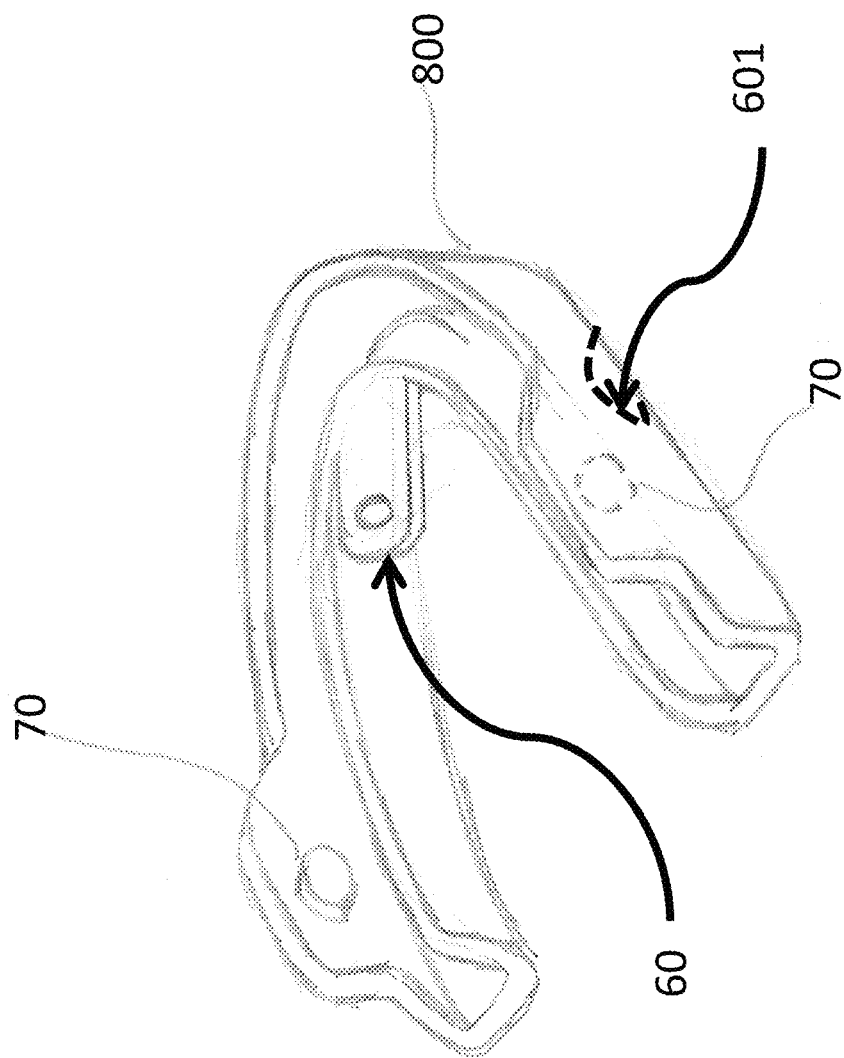
FIG. 12 is an isometric view of an embodiment of an oral attachment device.

FIG. 12 shows an embodiment of the internal oral unit 800 including convex electrodes 60 configured to contact the center of the hard palate, and concave electrodes 70 configured to contact the gums. The internal oral unit 800 may be a mouth-guard platform which may incorporate a bio-compatible adhesive to maintain contact with the dentition and/or oral tissue similar to a denture adhesive. In some embodiments the internal oral unit 800 electronic circuits 601 that perform some or all of the functions described above. The electrodes may be positioned in the structure which provides a slight spring force against the gums and hard palate to ensure electrode contact with oral tissue.

Figure 13:
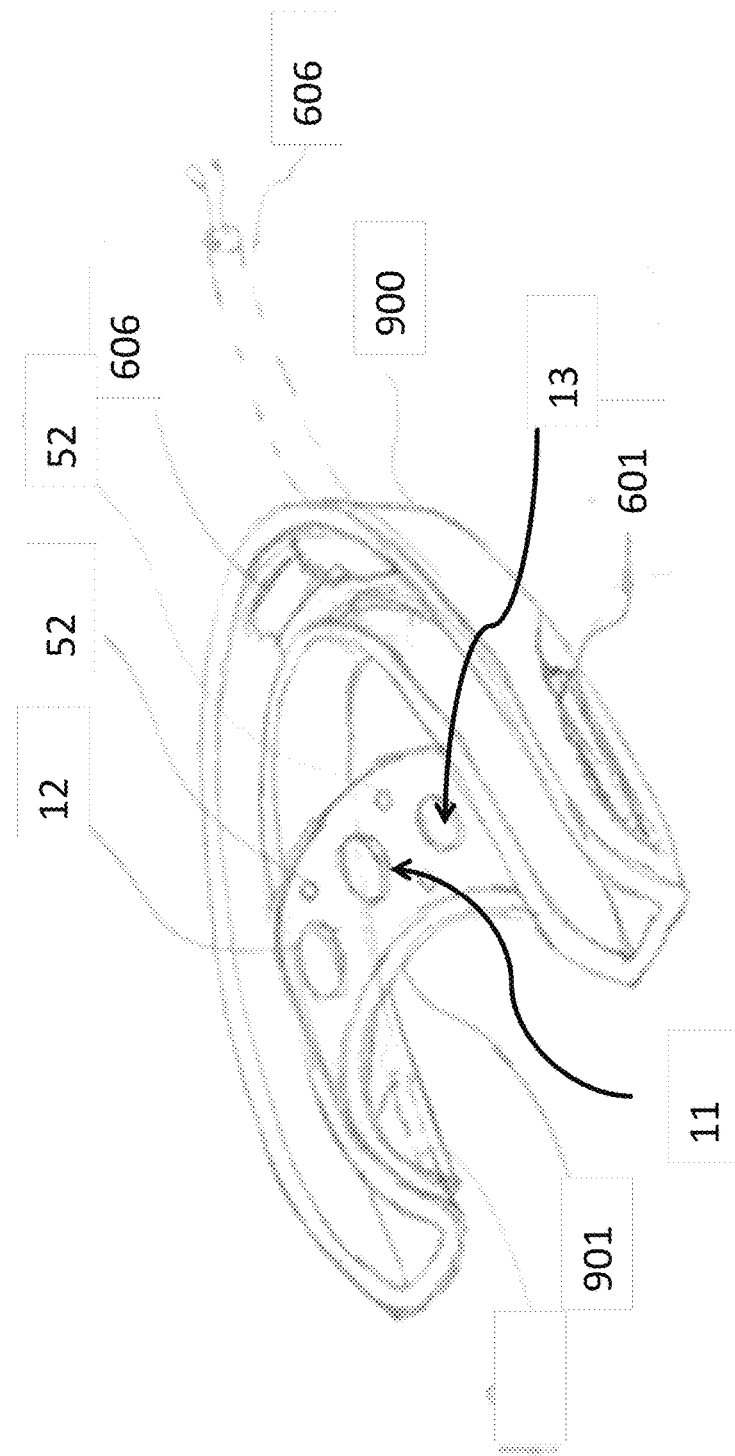
FIG. 13 is an isometric view of an embodiment of an oral attachment device.

FIG. 13 shows Oral attachment device 900, which incorporates a flexible transverse support band 901 to maintain contact with the hard palate and electrodes 11,12,13 and temperature sensor 52. Oral attachment device 900 may include electronics 601 and transmission unit 606.

Figure 14:
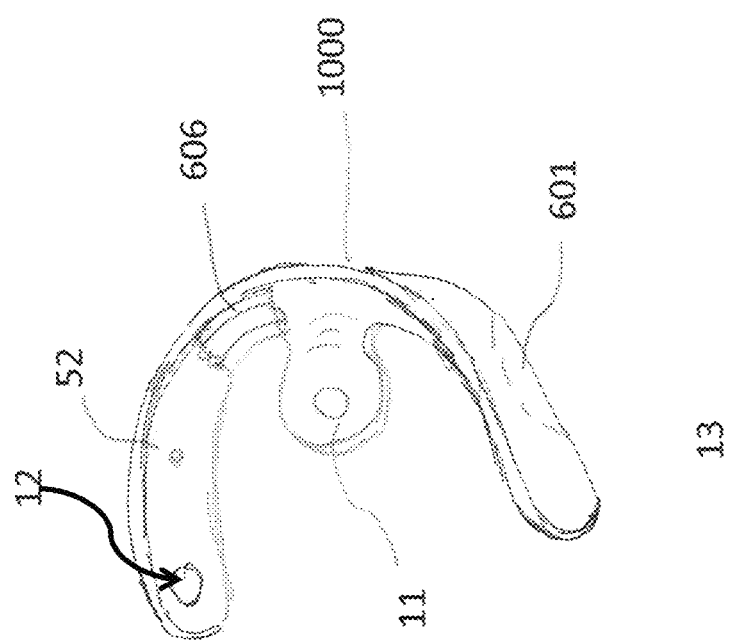
FIG. 14 is an isometric view of an embodiment of an oral attachment device.

FIG. 14 shows an oral attachment device 1000 which includes a thin flexible platform that incorporates a biocompatible adhesive to maintain contact with the mandible and flexible electronic circuits. The electrodes 11, 12 and 13 are positioned in the structure which provides a slight spring force against the gums and hard palate to ensure electrode contact with oral tissue. Some embodiments may include temperature 52, electronics 601 and transmission unit 606.

Figure 15:
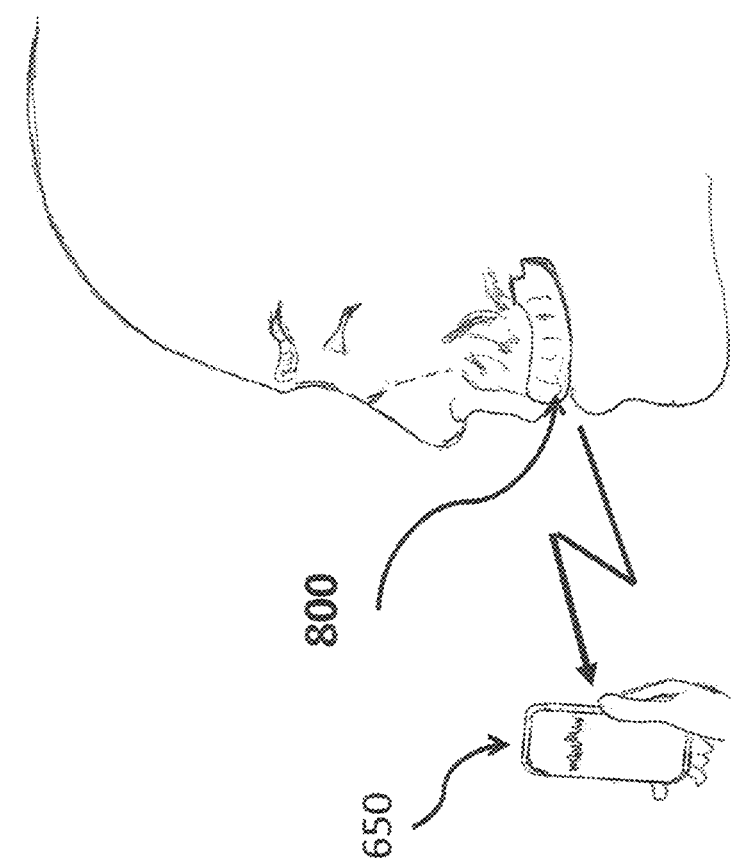
FIG. 15 is a sagittal view of a human head with the oral attachment device of FIG. 12 inserted in the oral cavity.

FIG. 15 shows a sagittal view of a human head with an example of an oral attachment mouthguard 800 with electrodes contacting the left and right side of the hard palate and one electrode contacting the hard palate and transmission system, and an exemplary embodiment of the external unit 650. External unit can be a smartphone, computer or other computing device.

An embodiment of the present invention may utilize subcomponent signals of the brain-based multicomponent bio-signals for screening, diagnosing and monitoring obstructive sleep apnea ("OSA"). OSA is a breathing disorder caused by movement and upper airway blockage by the tongue and narrowing of the upper airway by soft tissues within the nose, mouth and throat that occurs during sleep. This phenomenon causes snoring and recurrent interruption of breathing due to periodic obstruction of airflow in the upper airway during inhalation.

The current state of the art in diagnosing OSA and other sleep disorders involves using multichannel polysomnography to evaluate EEG, respiratory signals, cardiac signals, muscle tone, eye movements, and leg movements of a sleeping patient. This requires the cumbersome attachment of multiple EEG leads to the scalp, as well other transducers such as microphones, electrocardiograph ("ECG") electrodes, electromyograph ("EMG") electrodes and a pulse oximeter attached various parts of a patient. Devices intended for home use may measure fewer parameters are available, but still require multiple connections.

Embodiments of the invention enable detection of multicomponent brain-based bio-signals (FIG. 2) from which subcomponent bio-signals can be extracted including brain-based electrical activity including alpha or other waves (FIG. 3), eye movement (FIG. 5), respiration (FIG. 8) and ECG (FIG. 7). Brain electrical activity subcomponent signals can enable determination of sleep state/stage and overall sleep time. Respiration subcomponent bio-signals may enable determination of apnea events. Eye movement subcomponent bio-signals can enable determination of rapid eye movement (REM) sleep, and ECG subcomponent bio-signals can enable determination of heart rate during sleep. By analyzing the individual or combinations of these subcomponent bio-signals, either manually or with a computer system/program, a patient's sleep pattern may be determined to diagnose OSA.

In some embodiments, signal processing (including filtering, amplification, digitizing, storage etc.) and recording of some or all of the sub-component signals may occur in computer chip(s) embedded in an oral device including the sensor(s) can be accomplished. Resulting data can either be transmitted as it becomes available via wired or wireless technology (such as Bluetooth) to a receiving device (such as a smartphone, a computer, or dedicated device) and/or uploaded to a receiving device at a later time.

In other embodiments the multicomponent brain-based bio-signal is transmitted to an external receiving device (such as a smartphone, a computer, or dedicated device) for signal processing. The multicomponent brain-based bio-signal may be transmitted as it is being detected by the sensor or it may be recorded on a storage device in an oral device for retrieval at a later time.

If desired, in further embodiments the sensor detecting the multicomponent brain-based bio-signal may be supplemented with additional secondary sensors (i.e. accelerometers, thermocouples, $O_2$ saturation sensors, $CO_2$ sensors, air flow meters, etc.) may be used in combination with the multicomponent brain-based bio-signal to determine head position and oxygen desaturation and other events during sleep.

In some embodiments, the oral device may automatically turn off when it is removed from the patient's mouth. In other embodiments the oral device may be turned off manually. The signals stored on the device may then be uploaded to a computer system including a software program for interpretation of the signal data, and be available for a diagnosis to be made by a physician or other medical personnel.

In some embodiments, the electrical brain activity subcomponent signals extracted from the detected brain-based multi-component signal may be used along with signals from accelerometers to detect traumatic brain injury in military personnel, sports participants, or other people in at-risk professions or activities, such as concussions, strokes and seizures. Detection of traumatic brain injury may be facilitated by comparing current subcomponent signals to pre-existing baseline signals. The pre-existing baseline signals may be recorded from the specific patient being tested or a generic baseline derived from consolidation of multiple previously recorded signals from the patient or a segment of the population. In other embodiments these signals may be used to monitor performance.

In some embodiments, subcomponent signals extracted from the detected brain-based multi-component signal may be used to optimize training and provide feedback on performance of athletes and soldiers in order to enhance their capabilities during competition or in the field. The subcomponent signals extracted from the detected brain-based multi-component signal may also be used in biofeedback applications.

In another embodiment, brain waves and muscle activity subcomponent signals extracted from the detected brain-based multi-component signal may be used to determine the level of consciousness of a patient under general anesthesia.

In another embodiment, subcomponent signals extracted from the detected brain-based multi-component signal may be used to detect abnormal brain wave patterns indicative of hypoglycemia in persons with diabetes.

In another embodiment, brain-based bio-signals, eye movement, head position and breathing signals and other subcomponent signals extracted from the detected brain-based multi-component signal may be used to assist individuals who are physically impaired but mentally capable to operate a wide variety of equipment and tools using a brain-computer interface which interprets the subcomponent signals to operate a variety of equipment's actions. For example moving a motorized wheel chair or operating an artificial limb.

In another embodiment brain waves and eye movement subcomponent signals extracted from the detected brain-based multi-component signal can be monitored for advertising or media programming evaluation.

In another embodiment, a user can be trained to alter his brain waves in order to send a subcomponent signal extracted from the detected brain-based multi-component signal to a central computer in order to automatically control his mobile telephone, video game console, television set, music system or DVD player; change the temperature settings in the room; control an alarm system; control kitchen appliances; or control an automobile's computer system. For example, subcomponent signal extracted from the detected brain-based multi-component signal may be used to detect drowsiness or sedatives or drug related impairment in the operator of a motor vehicle by monitoring sub-component signals related to respiration, eye movement, and other useful parameters. The device for this application may be in the form of a nose clip, a mouthpiece, or combinations thereof that collects and processes brain-based multi-component signal via an onboard computer that can subsequently trigger alarm systems and provide notification, or alarm when a driver becomes a drowsy or falls asleep at the wheel.

In another embodiment, a device may utilize subcomponent signal extracted from the detected brain-based multi-component signal, such as eye movement and other bio-signals to control machines such as automobiles or airplanes using thought control especially for complex, rapid or emergency maneuvers. For example one application may be enhancing combat or drone pilots reaction times and assist in the control of aircraft during high-performance or wartime situations.

In an alternative embodiment of the system, the sensor and/or other elements of the system may be implanted in soft tissue, such as the soft palate or gums; or alternatively inside teeth or tooth implants; or in a third alternative, in parts of the body other than the oral cavity. For example the sensor and/or other elements of the system can be implanted in the soft palate and self-powered via piezoelectric material within the device. Or in another example the sensor and/or other elements of the system may be implanted beneath the skin and periodically charged inductively, capacitively, optically or other charging methods.

In another alternative embodiment, the sensor and/or other elements of the system may be located in a swimmer's or underwater diver's mouthpiece.

In third alternative embodiment, the sensor and/or other elements of the system may be mounted on a nose clip designed for comfortable placement within the nostrils of an individual.

Though many of the embodiments described herein describe applications in the oral cavity; the systems and methods described herein may also be applied to other internal tissues accessed through orifices or incisions in the body.

In the preceding specification, various preferred exemplary embodiments have been described with reference to the accompanying drawings. It will, however, be evident that various modifications and changes may be made thereto, and additional exemplary embodiments may be implemented, without departing from the broader scope of the invention as set forth in the claims that follow. The specification and drawings are accordingly to be regarded in an illustrative rather than restrictive sense.

What is claimed is:

1. A system for detecting a multicomponent brain-based electromagnetic bio-signal comprising:
   at least two bio-signal sensors embedded within walls of an oral attachment device configured to be positioned in an oral cavity to bring into contact the at least two bio-signal sensors with an oral tissue, wherein the at least two bio-signal sensors include at least two concave bio-signal electrodes configured to contact gums or at least two convex bio-signal electrodes configured to contact hard palate tissue; and
   a computer processing unit communicatively coupled to the at least two bio-signal sensors, wherein the at least two bio-signal sensors are configured to detect a raw oral multicomponent electromagnetic bio-signal at the oral tissue and send the raw oral multicomponent electromagnetic bio-signal to the computer processing unit, said computer processing unit includes an independent component analysis processor that isolates at least one primary raw brain-based multicomponent electromagnetic bio-signal from a plurality of other subcomponents within the raw oral multicomponent electromagnetic bio-signal, and wherein said computer processing unit further includes a plurality of brain wave band pass filters that are configured to further separate the raw brain-based multicomponent signal into a plurality of frequency brain wave bands.

2. The system of claim 1, further comprising a temperature sensor attached to the oral attachment device.

3. The system of claim 1, wherein the oral attachment device is configured to engage teeth.

4. The system of claim 1, wherein the at least two bio-signal sensors include concave electrodes configured to contact gums.

5. The system of claim 1, wherein the at least two bio-signal sensors include convex electrodes configured to contact hard palate tissue.

6. The system of claim 1, wherein the at least one primary raw brain-based multicomponent bio-signal correlates with electroencephalogram signal data.

7. The system of claim 6, wherein the at least two bio-signal sensors are configured to send the raw oral multicomponent electromagnetic bio-signal to the computer processing unit and wherein the computer processing unit is configured to generate a command based on data from a brain wave band filtered from the at least one primary raw brain-based multicomponent bio-signal.

8. The system of claim 7, wherein the at least two bio-signal sensors are configured to send the raw oral multicomponent electromagnetic bio-signal to the computer processing unit and wherein the computer processing unit is configured to generate a diagnosis of a condition following comparing data from a brain wave band filtered from the at least one primary raw brain-based multicomponent biosignal to predetermined baseline data for diagnosis of the condition.

9. The system of claim 8, wherein the condition is at least one of obstructive sleep apnea, concussion and seizure.

10. The system of claim 1, wherein the at least two bio-signal sensors are configured to send the raw oral multicomponent electromagnetic bio-signal to the computer processing unit and wherein the computer processing unit is configured to generate a command based on data from a brain wave band filtered from the at least one primary raw brain-based multicomponent bio-signal.

11. The system of claim 10, wherein the at least two bio-signal sensors are configured to send the raw oral multicomponent electromagnetic bio-signal to the computer processing unit and wherein the computer processing unit is configured to generate a diagnosis of a condition following comparing data from a brain wave band filtered from the at least one primary raw brain-based multicomponent biosignal to predetermined baseline data for diagnosis of the condition.

12. The system of claim 11, wherein the condition is at least one of obstructive sleep apnea, concussion and seizure.

13. The system of claim 12, wherein the wherein the oral attachment device is configured to engage teeth.

14. The system of claim 13, wherein the oral attachment device includes concave electrodes configured to contact the at least two bio-signal sensors to gums.

15. The system of claim 13, wherein the oral attachment device includes convex electrodes configured to contact the at least two bio-signal sensors to hard palate tissue.

16. The system of claim 1, wherein the at least two bio-signal sensors are configured to send the raw oral multicomponent electromagnetic bio-signal to the computer processing unit and wherein the computer processing unit is configured to generate a diagnosis of a condition following comparing data from a brain wave band filtered from the at least one primary raw brain-based multicomponent biosignal to predetermined baseline data for diagnosis of the condition.

17. The system of claim 16, wherein the condition is at least one of obstructive sleep apnea, concussion and seizure.

18. The system of claim 17, wherein the oral attachment device is configured to engage teeth.

19. The system of claim 18, wherein the oral attachment device includes concave electrodes configured to contact the at least two bio-signal sensors to gums.

20. The system of claim 18, wherein the oral attachment device includes convex electrodes configured to contact the at least two bio-signal sensors to hard palate tissue.

\* \* \* \* \*